US00PP23882P3

(12) United States Plant Patent
Goffreda et al.

(10) Patent No.: US PP23,882 P3
(45) Date of Patent: Sep. 10, 2013

(54) NECTARINE TREE NAMED 'NJN101'

(50) Latin Name: ***Prunus persica* L.**
Varietal Denomination: NJN101

(75) Inventors: Joseph C. Goffreda, Millstone Township, NJ (US); Anna M. Voordeckers, East Windsor Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 13/200,068

(22) Filed: Sep. 16, 2011

(65) Prior Publication Data

US 2013/0074226 P1 Mar. 21, 2013

(51) Int. Cl.
*A01H 5/00* (2006.01)

(52) U.S. Cl.
USPC ..... Plt./190

(58) Field of Classification Search
USPC ..... Plt./190
See application file for complete search history.

*Primary Examiner* — Kent L Bell
(74) *Attorney, Agent, or Firm* — James A. Lucas; Driggs, Hogg, Daugherty & Del Zoppo Co., LPA

(57) ABSTRACT

A new and distinct nectarine variety of *Prunus persica* named 'NJN101' is provided. This variety is distinguished from other nectarine varieties by its unique combination of showy flowers, fruit that ripen in early-season, glossy fruit with an attractive red over color and orange red ground color, clingstone fruit with a juicy, melting texture and sweet, moderately acidic flavor, and excellent production of firm fruit that maintain their eating quality following cold storage.

6 Drawing Sheets

Latin name of genus and species of the plant claimed: *Prunus persica* L.

Variety denomination: 'NJN101'.

CROSS REFERENCE TO RELATED APPLICATIONS

NONE

STATEMENT REGARDING FEDERALLY SPONSORED RESEARCH OR DEVELOPMENT

NONE

BACKGROUND OF THE INVENTION

The present invention relates to a new and distinct variety of nectarine tree named 'NJN101'. Our new tree resulted from crossing B8-9-46-712034 as the seed parent with 'Eastern Glo' nectarine tree, as the pollen parent. The new variety differs from seed parent B8-9-46-712034 (unpatented) in that the new variety has large, showy flowers and firm, yellow-orange fleshed fruit with an attractive, glossy finish, while the seed parent has small, non-showy flowers and comparatively soft, greyed-white fleshed fruit that usually have a poor finish. The new variety differs from pollen parent 'Eastern Glo' (U.S. Plant Pat. No. 7,890) in that the new variety has been cold hardy to about −20° C. and has good eating quality, while the pollen parent has had light crops after exposure to −20° C. and generally has fair eating quality. In comparison to the commercial nectarine variety 'Summer Beaut' (U.S. Plant Pat. No. 4,093), the fruit of the new variety has a warm orange-red ground color and matures approximately 12 days earlier. The resulting tree was selected when growing in a cultivated area located at a fruit research center in Cream Ridge, N.J.

BRIEF SUMMARY OF THE INVENTION

The 'NJN101' variety is distinguished from other nectarine varieties due to the following unique combination of characteristics:

- Round fruit with a low tendency to split for the season.
- Glossy fruit with an attractive red over color and orange-red ground color.
- Excellent production of firm fruit that ripen in early-season.
- Fruit with a good to very good eating quality.

The variety was asexually reproduced at a fruit research center in Cream Ridge, N.J. Asexual reproduction of this new variety by budding onto 'Lovell' rootstock (unpatented) shows that the foregoing characteristics are so reproduced.

The following detailed description concerns the original tree, 'NJN101'. The original tree and asexual progeny have been observed growing in a cultivated area at the fruit research center in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions, unless the context clearly indicates otherwise. Color designations are made with reference to The Royal Horticultural Society (R.H.S.) Colour Chart. (1966 Edition)

BRIEF DESCRIPTION OF THE DRAWINGS

This new variety is illustrated by the accompanying photographic drawings, depicting the nectarine tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
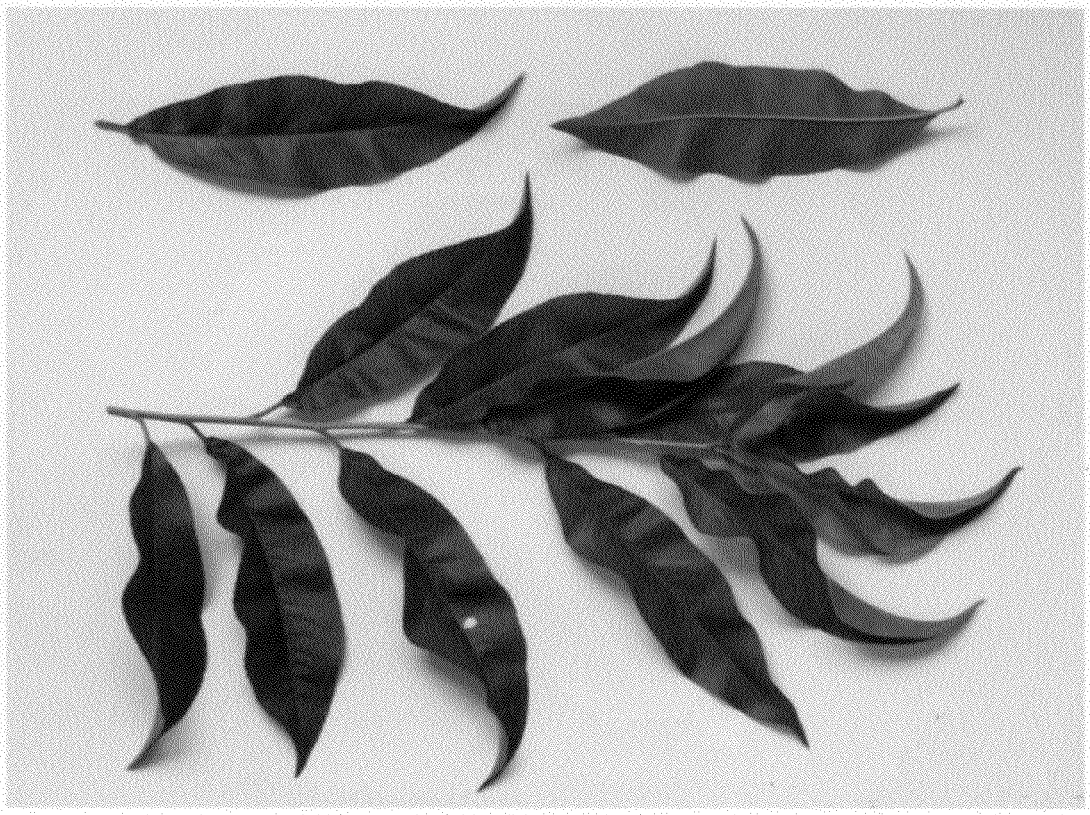
FIG. 1 is a color photograph taken on Jun. 14, 2011 of a characteristic twig of 'NJN100' in the late spring bearing typical leaves of the foliage.
Figure 2:
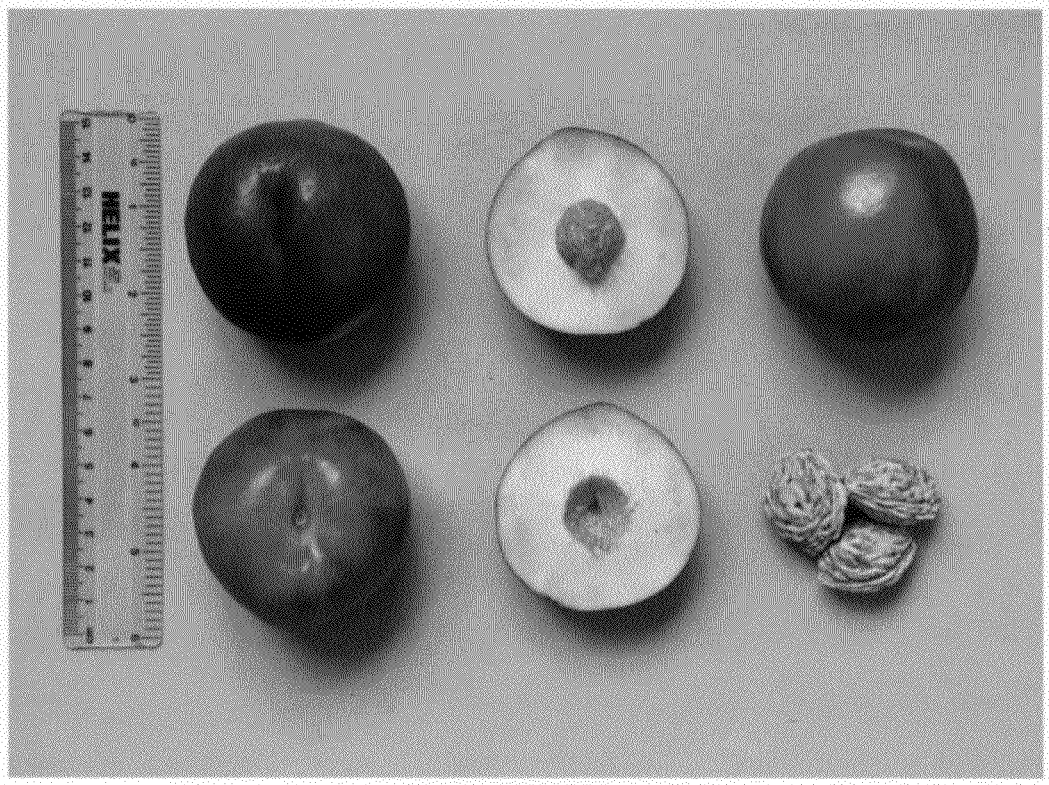
FIG. 2 is a color photograph taken on Jul. 16, 2004 of characteristic mature fruit and stones of 'NJN101'. Whole fruit are presented in three positions and a transverse cross section to show that the pericarp tends to adhere to the pit when the fruit is mature. The stones illustrate the ovate shape and the pit grooves on the surface of the stone.
Figure 3:
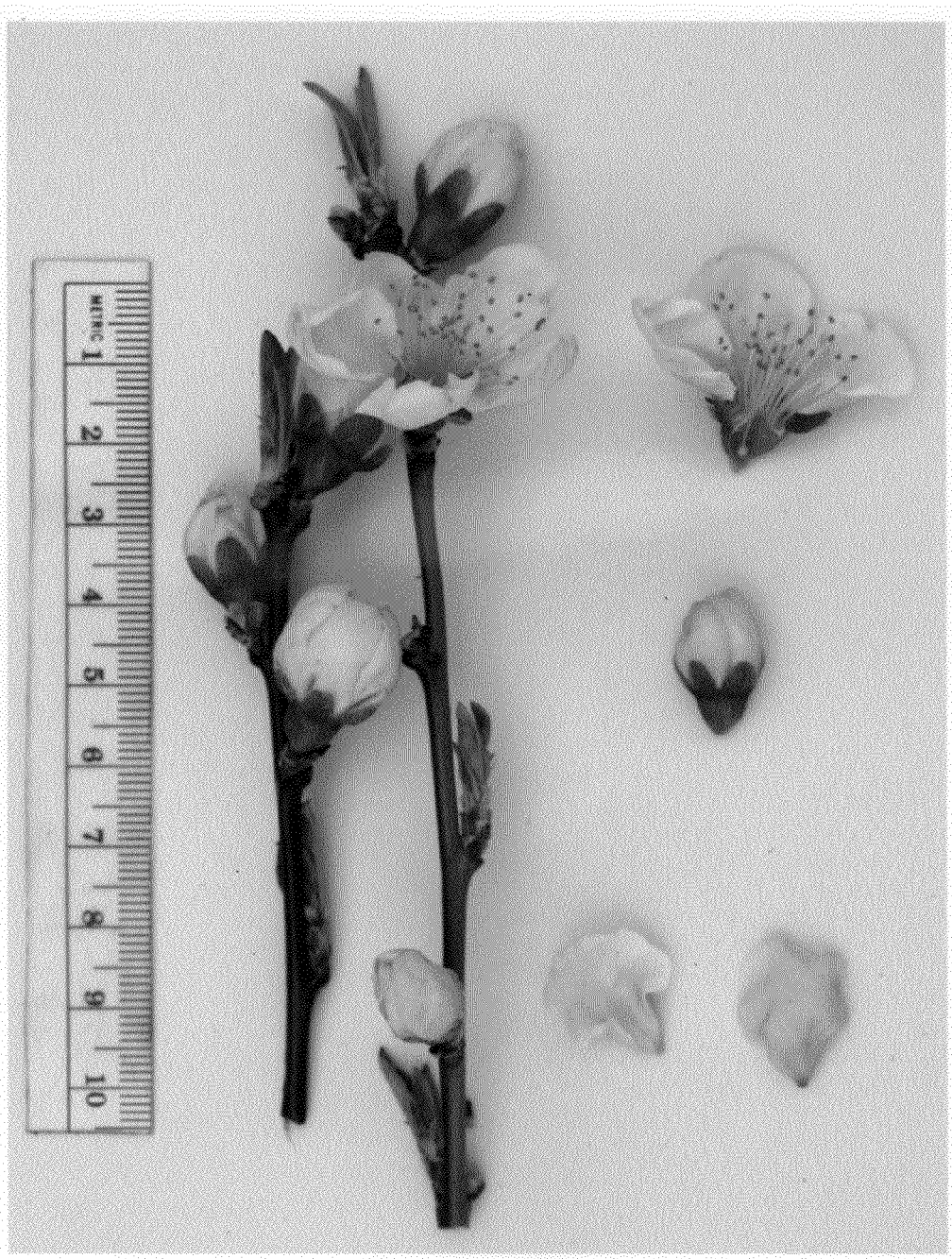
FIG. 3 is a color photograph of a characteristic twig that illustrates the typical flower buds and large, showy flowers of 'NJN101' observed on a tree that was 6 years of age on Apr. 21, 2004.
Figure 4:
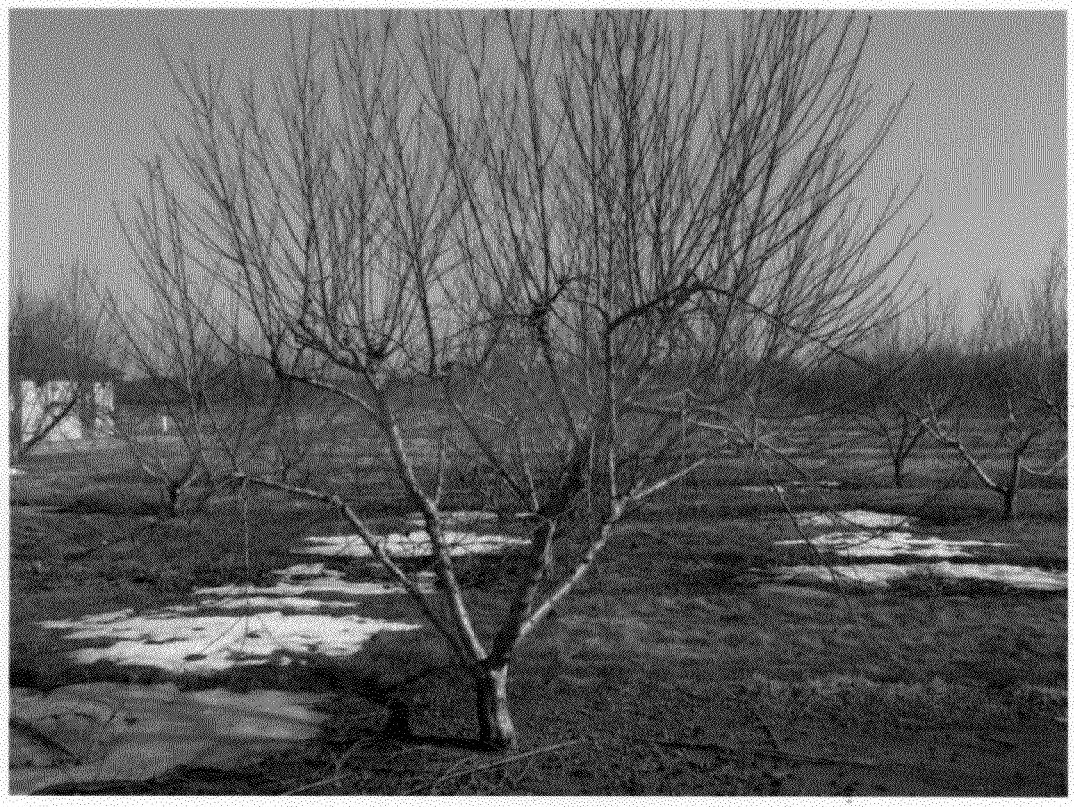
FIG. 4 is a color photograph of a dormant tree of 'NJN101', prior to pruning, in late winter that illustrates the rounded, slightly upright growth habit of a tree at the fruit research center in Cream Ridge, N.J. on Feb. 17, 2011.
Figure 5:
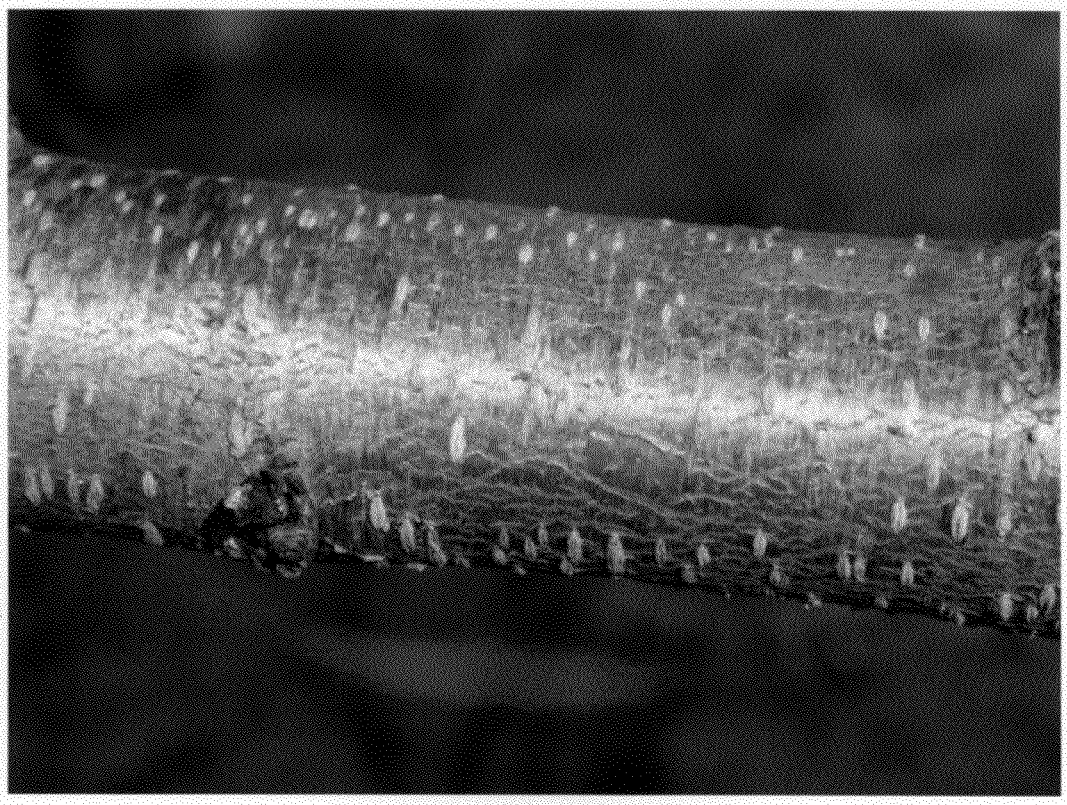
FIG. 5 is a color photograph taken on Feb. 17, 2011 of immature bark of 'NJN101' that illustrates color and the moderately high density of conspicuous lenticels on the immature bark.
Figure 6:
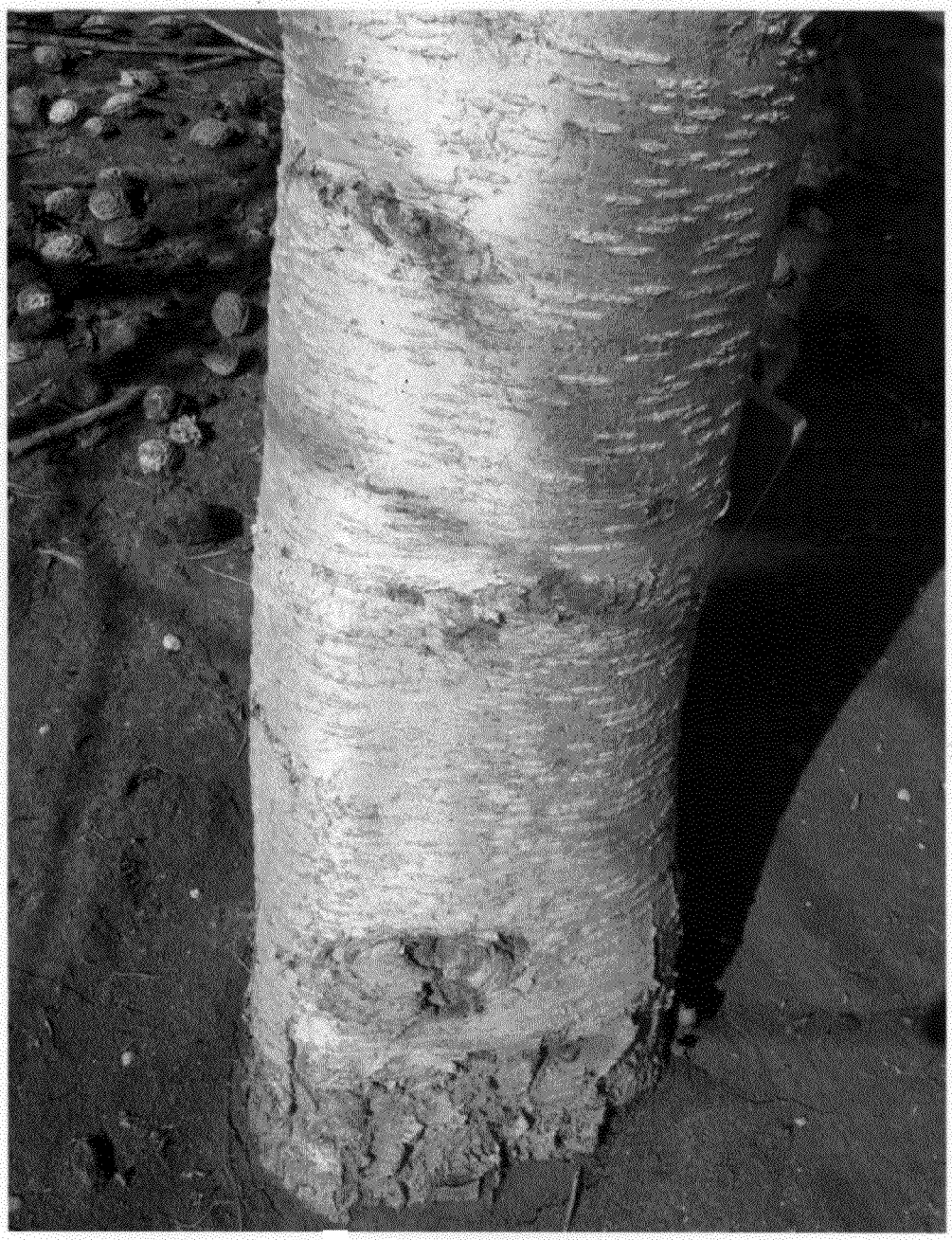
FIG. 6 is a color photograph taken on Feb. 17, 2011 of mature bark of 'NJN101' that illustrates the moderately smooth texture and conspicuous elliptical lenticels of the mature bark.

The colors and illustration of this type may vary with lighting and other conditions and, therefore, color characteristics of this new variety should be determined with reference to the observations described herein, rather than from these illustrations alone.

DETAILED BOTANICAL DESCRIPTION

The following detailed description of the 'NJN101' variety is based on observations of an asexually reproduced tree. The observed tree was six years of age and growing on 'Lovell' seedling rootstock (unpatented) in the fruit research center in Cream Ridge, N.J.

Scientific name: *Prunus persica* L.

Parentage:

*Seed parent*.—B8-9-46-712034.

*Pollen parent*.—'Eastern Glo'.

Tree:

*Vigor*.—Vigorous.

*Plant hardiness zone*.—Growth of plants has only been observed in zone 6b.

*Dormant flower bud cold tolerance*.—At least to −20° C.

*Overall shape*.—Rounded, slightly upright.

*Height*.—Slightly above average as compared to other nectarine cultivars. For example, measurement of a typical grafted tree on 'Lovell' seedling rootstock (unpatented) at six years after planting shows an average height of 4.0 meters when grown in Cream Ridge, N.J.

*Width*.—Slightly below average as compared to other nectarine cultivars. For example, measurement of a typical grafted tree on 'Lovell' seedling rootstock (unpatented) at six years after planting shows an average width of 4.2 meters when grown in Cream Ridge, N.J.

*Caliper*.—Six year old tree is 44 cm in circumference measured at 20 cm from the ground.

Trunk and branches:

*Trunk bark texture*.—Moderately smooth texture with conspicuous elliptical lenticels.

*Trunk bark color*.—Greyed-white (RHS 156A).

*Primary branches*.—Branches that are approximately 18 cm in circumference are greyed-orange (RHS 177C) in color, overlaid with greyed-green (RHS 197D). The branch angles range from 38 to 50 degrees, averaging about 45 degrees. Lenticels: High density, approximately 3.6 per square cm; lanceolate in shape and conspicuous; typical examples of which measured 3.4 mm in length and 0.7 mm in width; greyed-orange (between RHS 165C and RHS 165D) in color and bordered with grey-brown (RHS 199D). Branch pubescence: None. New growth bark: Greyed-purple (RHS 183B) in sun; color yellow-green (between RHS 152A and RHS 152C) in shade.

*Internodes*.—Length averaging 25.0 mm on a one-year shoot.

Leaves:

*Texture*.—Glabrous.

*Sheen*.—Young leaves semi-glossy with a flat finish on the underside. Adaxial surface of mature leaves are generally smooth, glabrous, and slightly glossy. Abaxial surface of mature leaves are nearly smooth, glabrous, with a matte finish.

*Length*.—About 172 mm to 210 mm, averaging about 194 mm including the petiole.

*Width*.—About 39 mm to 49 mm, averaging about 45 mm.

*Petiole*.—Averaging 12.1 mm long and about 1.5 mm in diameter.

*Margin*.—Serrulate.

*Margin undulation*.—Slight.

*Form*.—Lanceolate.

*Apex*.—Acuminate, curved downward.

*Base*.—Cuneate.

*Venation*.—Pinnate.

*Glands*.—Number: About 0 to 3, averaging about 1.7. Position: Generally, located on the leaf margin. Size: Length averaging 1.1 mm and width averaging 0.9 mm. Form: Reniform.

*Stipules*.—None observed on mature leaves.

*Leaf color*.—Upper leaf surface: Yellow-green (between RHS 146A and RHS 147A). Lower leaf surface: Yellow-green (RHS 148B). Vein: Greyed-yellow (RHS 160A).

*Pubescence*.—None.

Flowers:

*Size*.—Medium to large size, typical flower measuring between 27 mm to 33 mm, averaging about 30 mm across.

*Color*.—Dormant bud: Grey (between RHS 201A to RHS 201D). Pink stage bud: Red-purple (between RHS 62C). Open flower: Red (between RHS 62C and RHS 62D).

*Petals*.—Typically five petals per flower; cupped, nearly round, margin entire, petals may undulate near the margin, especially on freshly open flowers; averaging about 17.8 mm long and 17.0 mm wide.

*Petal apex*.—Obtuse, nearly rounded.

*Petal base*.—Cuneate.

*Stamens*.—Number: Variable, typical range 38 and 44, averaging 41.6. Length: Variable, between 19.1 mm to 26.1 mm, averaging 23.1 mm. Filament color:

White (between RHS 157A). Anther color: Red (between RHS 46B and RHS 46C).

*Pistil*.—Number: One. Size: Length between 1.3 and 18.1 mm, averaging about 17.0 mm. Pistil color: Yellow-green (between RHS 145A and RHS 145B). Ovary: Glabrous and ellipsoid in shape.

*Sepals*.—Number: Five. Pubescence: Length short to long, with moderate to high density, increasing toward the edge. Color: Yellow-green (RHS 146C) with a greyed-purple (between RHS 183C and RHS 183D) over color. Shape: Triangular, with a rounded apex. Size: Length averaging 5.4 mm, width averaging 5.0 mm.

*Nectar cup color*.—Greyed-orange (RHS 168B).

*Pollen*.—Abundant; yellow (RHS 11A) in color.

*Fragrance*.—Very slight.

*Bloom season*.—Onset of bloom in 2005 on April 17; full bloom on April 19.

Fruit:

*Size*.—Medium to large, averaging about 6.2 cm long, 6.5 cm wide parallel to the suture and 6.3 cm wide perpendicular to the suture.

*Typical weight*.—146 g.

*Form*.—Longitudinal section: Round. Traverse section: Round.

*Suture*.—Very shallow, extending from the base to apex.

*Ventral surface*.—Typically smooth.

*Base*.—Flat.

*Apex*.—Round, slightly depressed.

*Stem*.—Average length of 2.9 mm and an average diameter of 3.6 mm.

*Skin*.—Thickness: Average. Surface: Glabrous, typically glossy. Tenacity: Average. Astringency: None. Tendency to crack: Low. Color: Mottled red (RHS 53A) over a red (RHS 45A) blush; ground color orange-red (RHS 30D).

*Fruit properties*.—Flesh color: Yellow-orange (RHS 16B) becoming yellow (RHS 9B), toward the stone. Flesh adhesion: Clingstone. Juice: Moderate. Texture: Firm, but melting. Fibers: Not noticeable. Ripens: Between July 12 and July 29 at Cream Ridge, N.J. Flavor: Typically sweet and moderately acidic. Soluble solids: 11.6%. Aroma: Slight. Eating quality: Good to very good.

*Keeping quality*.—Above average. Has held its flavor and firmness for at least 14 days in cold storage at 1° C. to 4° C.

*Shipping quality*.—Very good. Fruit are generally very firm at harvest. No bruising or scaring disorders have been observed.

*Usage*.—Dessert.

*Market*.—Local and long distance.

*Productivity*.—Excellent. Trees have produced a crop in 10 out of 10 years and a full crop in eight out of 10 years at Cream Ridge, N.J.

Stone:

*Type*.—Clingstone.

*Form*.—Ovate.

*Base*.—Medium.

*Apex*.—Medium.

*Surface*.—Pit grooves.

*Ventral suture*.—Medium.

*Dorsal ridge*.—Medium height, narrow width, forming lines of medium depth.

*External color*.—Greyed-orange (between RHS 165C and 165D).

*Internal color when cracked*.—Greyed-orange (RHS 164D).

*Cavity surface color*.—Greyed-orange (RHS 164C).

*Average stone dry weight*.—4.9 g.

*Average stone wall thickness*.—Varies between 5.0 mm along the ventral suture and 8.1 mm at the base.

*Size*.—Averages about 30.7 mm long, 24.4mm wide parallel to the dorsal ridge, and 19.5 mm wide perpendicular to the dorsal ridge.

*Tendency to split*.—Low.

*Kernel*.—Form: Highly variable; forms only rudimentary seed. Skin color: Greyed-orange (between RHS 165B and RHS 165C). Vein color: Greyed-orange (RHS 165B). Viability: No. Size: Highly variable; forms only rudimentary seed.

Plant/fruit disease and pest resistance/susceptibility: No atypical resistances/susceptibilities have been noted under normal cultural practices.

We claim:

1. A new and distinct variety of nectarine tree, substantially as herein shown and described.

* * * * *